(12) United States Patent
Harkin et al.

(10) Patent No.: US 10,126,290 B2
(45) Date of Patent: Nov. 13, 2018

(54) TEST TAPE DEVICE AND OPERATING METHOD

(71) Applicant: Roche Diabetes Care, Inc., Indianpolis, IN (US)

(72) Inventors: Thomas Harkin, Bristol (GB); Liang Yi Li, New Taipei (CN); Hans List, Hesseneck-Kailbach (DE); Wolfgang Rödel, Heidelberg (DE); Klaus Thome, St. Leon-Rot (DE); Wen Tsung Wang, Fengyuan (TW); Karl Werner, Heidelberg (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 286 days.

(21) Appl. No.: 15/016,944

(22) Filed: Feb. 5, 2016

(65) Prior Publication Data

US 2016/0153962 A1 Jun. 2, 2016

Related U.S. Application Data

(63) Continuation of application No. PCT/EP2014/067118, filed on Aug. 8, 2014.

(30) Foreign Application Priority Data

Aug. 9, 2013 (EP) .................................... 13179963

(51) Int. Cl.
*G01N 33/487* (2006.01)

(52) U.S. Cl.
CPC ... *G01N 33/48764* (2013.01); *G01N 2400/00* (2013.01)

(58) Field of Classification Search
CPC ............................................... G01N 33/48764
See application file for complete search history.

(56) References Cited

U.S. PATENT DOCUMENTS

| 2010/0249567 A1 | 9/2010 | Harttig et al. |
| 2012/0004852 A1* | 1/2012 | Miltner ............ G01N 33/48764 |
| | | 702/19 |
| 2013/0062202 A1 | 3/2013 | Riebel et al. |

FOREIGN PATENT DOCUMENTS

WO WO 2012/080384 A1 6/2012

OTHER PUBLICATIONS

International Search Report, PCT/EP2014/067118, dated Nov. 4, 2014.

(Continued)

*Primary Examiner* — Robert R Raevis
(74) *Attorney, Agent, or Firm* — Bose McKinney & Evans LLP (57) ABSTRACT

Disclosed is a test tape device comprising a housing having a cassette compartment for a replaceable tape cassette, a cassette door which can be retained in a closed position and which allows access to the cassette compartment through a housing opening in an open position, a tip cover which can be positioned in a first position covering a housing aperture and a second position allowing access to a tip of the tape cassette, wherein the tip cover is moveable to a third position in which the cassette tip is at least partially uncovered and the housing opening is extended into the area of the cassette tip, and wherein the cassette door is self-opening when moving the tip cover to the third position.

16 Claims, 6 Drawing Sheets

(56) References Cited

OTHER PUBLICATIONS

International Preliminary Report on Patentability and Written Opinion of the International Search Authority, PCT/EP2014/067118, dated Feb. 9, 2016.

* cited by examiner

TEST TAPE DEVICE AND OPERATING METHOD

RELATED APPLICATIONS

This application is a continuation of PCT/EP2014/067118, filed Aug. 8, 2014, which claims priority to EP 13179963.7, filed Aug. 9, 2013, both of which are incorporated herein by reference in their entirety.

BACKGROUND

The invention concerns a test tape device in particular for blood glucose tests and further concerns a method for operating such a device.

Such devices can be designed as a glucose meter for the self-diagnosis of diabetics. A plurality of test fields is provided on a spoolable test tape in the tape cassette. The reactive test fields are examined photometrically after the application of a small amount of blood sample in order to determine the glucose content. The tape cassette is inserted as a disposable part into a compact hand-held device housing in order to allow the necessary analytical steps to be carried out automatically and rapidly.

WO 2012/080384 discloses a glucose meter having a door lock for retaining the cassette door in the closed position, wherein the protective cover is coupled with the door lock via an interlocking mechanism, whereby the door lock is blocked in the closed position of the protective cover and can be unlocked in the release position of the cover. The interlocking mechanism has a swivel-mounted lock catch which can be turned by manually operating the protective cover. Further, the door lock has a slider for manual operation. However, such function is not intuitively clear to the user, is difficult in handling and requires a complex construction. If the slider is operated in the closed or not fully opened position of the tip cover, the cassette door will not open and the user may get the false impression that the cassette door is jammed.

SUMMARY

On this basis this disclosure further improves the known test devices and methods of device operation to achieve a user-friendly, simple and straightforward producible design.

This disclosure is based on the idea of using only one operating element for enabling a cassette change. Accordingly, it is proposed according to this disclosure:
  a housing having a cassette compartment adapted to receive a replaceable analytical tape cassette,
  a cassette door which can be retained in a closed position preferably by a door lock and which allows access to the cassette compartment through a housing opening in an open position,
  a tip cover which can be positioned in a first (closed) position covering a housing aperture and a second (operating) position allowing access to a tip of the tape cassette arranged to protrude through the housing aperture for sample application,
  wherein the tip cover is moveable into a third (release) position in which the cassette tip is at least partially uncovered and the housing opening is extended into the area of the cassette tip,
  and wherein the cassette door is self-opening when moving the tip cover to the third position.

In this way the tape cassette can be easily removed without collision with the tip cover. As the cassette door is self-opening in the third position, it is required to handle only one functional element to move the tip cover into the third position. There is no need for the user to know the function of additional elements and the order of their use.

In a preferred embodiment the door lock is automatically unlocked when moving the tip cover to the third position, so that a self-acting opening of the cassette door is effectuated.

Another advantageous embodiment provides that the door lock can be unlocked by means of a manually activated release button, wherein the release button is mechanically connected to the tip cover to actuate a movement to the third position. In this way, the release button is the only operational element to be handled in case of a cassette exchange.

In order to further ease the operation, it is advantageous when a sliding module is connected to the release button, wherein the tip cover can be pivoted from the first position to the third position by a pull force of the sliding module.

It is also conceivable that the tip cover can be manually operated to assume the third position and at the same time forms a leverage to actuate the door lock. A further improvement can be achieved when a pivot is provided to allow pivoting of a free end of the tip cover.

In a further preferred embodiment the tip cover is movable in a guide structure between the first and second positions, wherein the guide structure is mounted on a slider which is movable relative to the housing, wherein a movement of the slider carries the tip cover to the third position and unlocks the door lock.

For an ergonomic design, it is particularly advantageous when a grip member is formed on the slider for shifting of the slider in a linear track of the housing.

A further manufacturing and functional simplification can be achieved when the tip cover is moveably connected to the cassette door to allow movement between the first and second positions, and when the cassette door and the tip cover can be moved cooperatively as a unitary lid to move the cassette door to the open position and the tip cover to the third position. In this context, it is further advantageous when a folding connection is provided as a hinge mounted between an edge of the cassette door and of the tip cover.

Another unique aspect of this disclosure is a test tape device comprising a housing having a cassette compartment adapted to receive a replaceable analytical tape cassette, a cassette door which can be retained in a closed position preferably by a door lock and which allows access to the cassette compartment through a housing opening in an open position, a tip cover which can be positioned in a first (closed) position covering a housing aperture and a second (working) position allowing access to a tip of the tape cassette arranged to protrude through the housing aperture for sample application, and further comprising a device electronics that is configured to prompt the user to open the tip cover for a cassette change and automatically unlocks the cassette door in the open position of the tip cover. In this way, there is no need for a specific user operation for opening the cassette door, and any confusion on the sequence of operation during the cassette change is avoided. Furthermore, a compact and robust design with a reduced number of mechanical elements can be achieved.

Preferably, the device electronics are adapted to detect conditions for replacement of the tape cassette, wherein said conditions comprise one of a consumed number of tests, a defect of the cassette and expiry of a life period of the cassette.

This disclosure is also directed to a test tape system comprising a test tape device according to this disclosure and an analytical tape cassette including a test tape inserted in the cassette compartment.

In order to achieve the results stated above with respect to a method of operation, the following measures are proposed:

positioning a tip cover in a first position for covering a housing aperture, moving the tip cover to a second position to allow access to a tip of the tape cassette for sample application, moving the tip cover to a third position in which the cassette tip is at least partially uncovered and the housing opening is extended into the area of the cassette tip, inserting or replacing the tape cassette in the third position of the tip cover, wherein the cassette door is self-opening.

In a preferred embodiment, tip cover is provided as an actuation element for automatically releasing a door lock of the cassette door in the third position.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein:

FIG. 4a is a rear view of a further embodiment of a tape cassette-type glucose meter illustrating three positions of the tip cover;

FIG. 4b is a partly expanded and cutaway side view showing a cassette door lock of the glucose meter of FIG. 4a;

DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

The drawings illustrate a test tape device configured as a portable glucose meter 10 for self-monitoring of blood glucose and comprising a housing 12 for inserting a disposable analytical tape cassette 14. The tape cassette 14 stores a number of test fields on a carrier tape which can be successively spooled forwards to a cassette tip 16 for a targeted application of a blood sample.

Figure 1A:
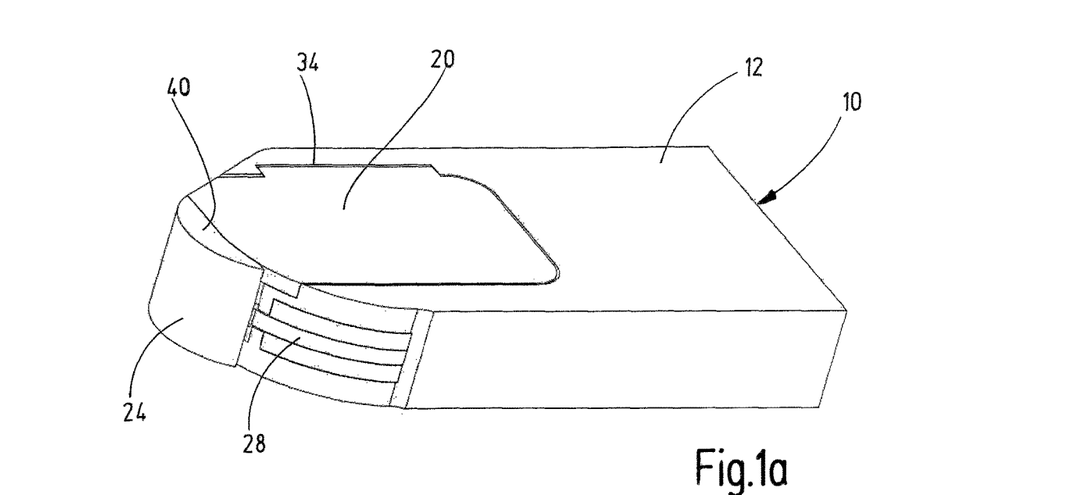
FIG. 1a is a perspective view of a tape cassette-type glucose meter in the closed position of both a cassette door and a tip cover.
Figure 1B:
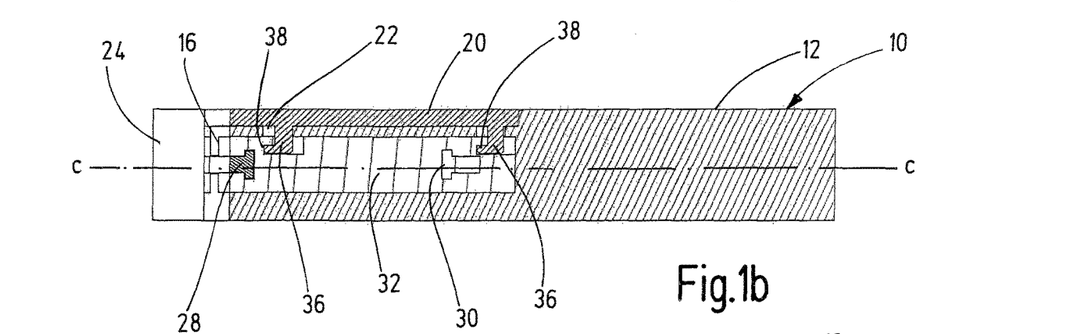
FIG. 1b is a sectional view of the device of FIG. 1a taken along line b-b of FIG. 1c.
Figure 1C:
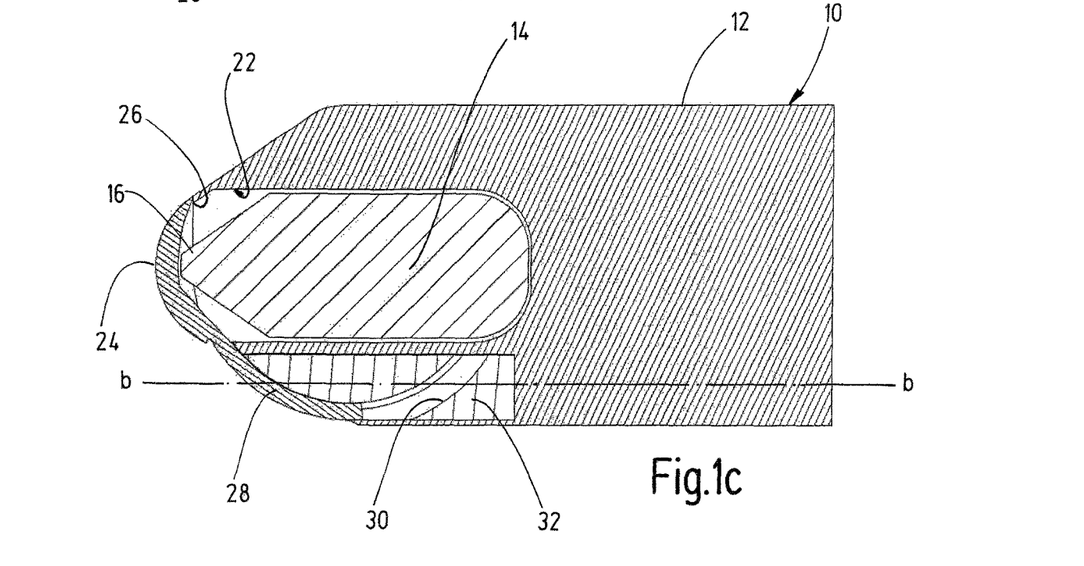
FIG. 1c is a sectional view of the device of FIG. 1a taken long line c-c of FIG. 1b.

As shown in FIGS. 1a-c the glucose meter 10 comprises a hinged cassette door 20 covering a cassette compartment 22 and a tip cover 24 protecting a lateral housing aperture 26 and the cassette tip 16 protruding therethrough. The tip cover 24 forms a shell over the cassette tip 16 and has an extension 28 which is guided in an arc-shaped conduit 30. This conduit 30 is formed in a guide block 32 slidably disposed in the housing 12.

The cassette door 20 on one side has a spring-loaded hinge 34 configured to swing open automatically when released to allow a change of cassette 14. In the state shown in FIG. 1, when the tip cover 24 is in the closed (first) position, the cassette door 20 is locked by retaining hooks 36 engaging into undercut recesses 38 of the guide block 32. Thus, the cassette 14 cannot be removed when the side wall 40 of the tip cover 24 in the closed position overlaps the cassette tip 16. In this way, accidental damage by the user is avoided.

Figure 2A:
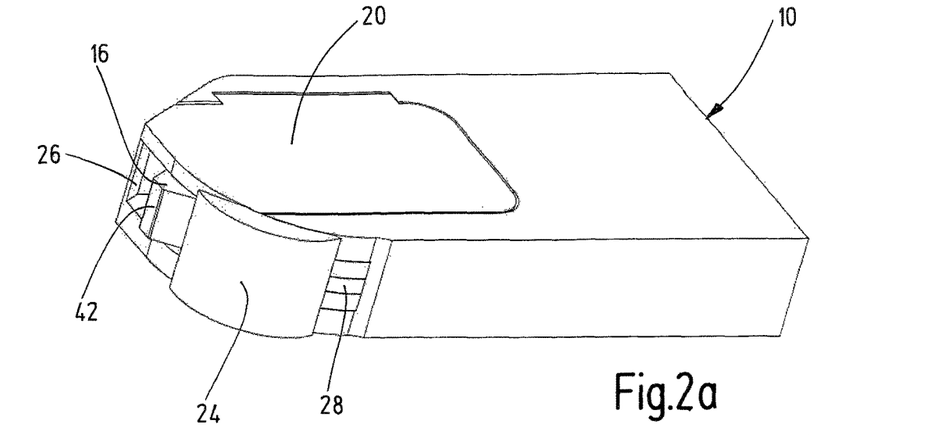
FIGS. 2a-2c show the glucose meter in a working position of the tip cover in views similar to FIG. 1.
Figure 2B:
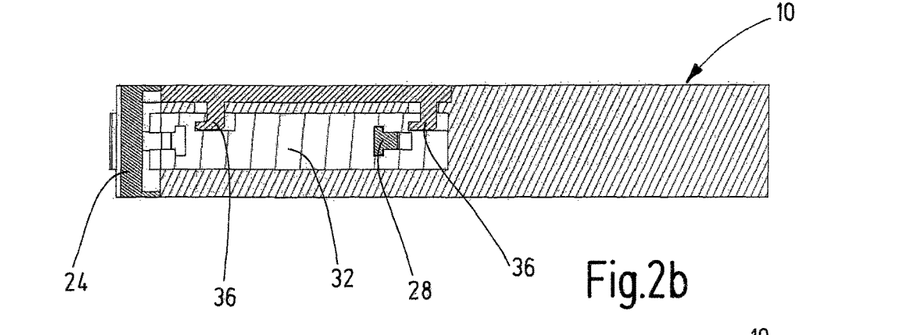
Figure 2C:
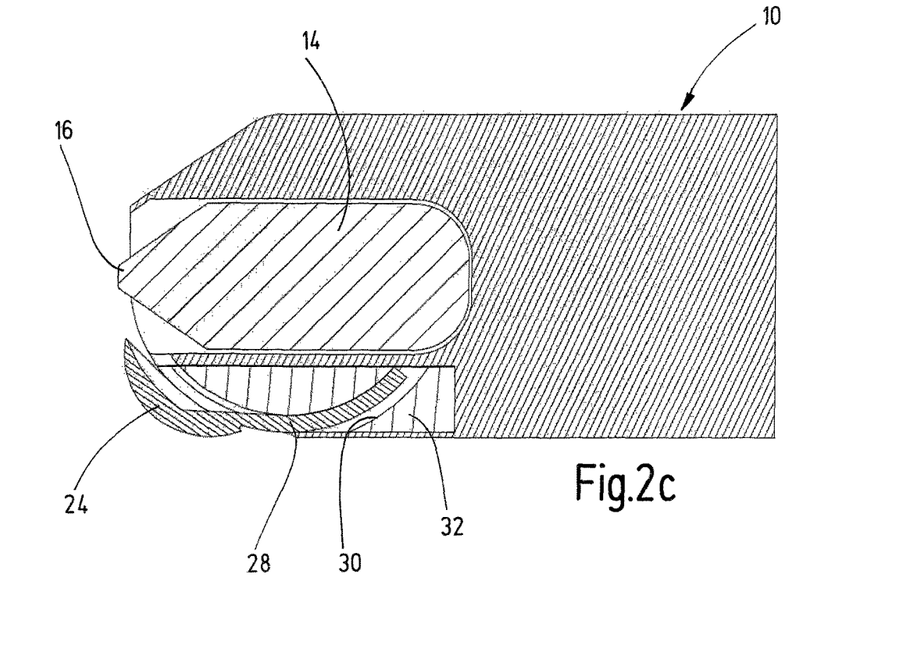

FIGS. 2a-c show the glucose meter 10 with the tip cover 24 in a second (operating) position. To attain this position, the extension 28 is moved on a curved path in the conduit 30 by appropriate manual actuation of the tip cover 24. In the second position of the tip cover 24, the carrier tape 42 guided above the cassette tip 16 is easily accessible for sample application, e.g., a blood drop from a fingertip. Still, the cassette door 20 is maintained in the closed position by retaining hooks 28.

Figure 3A:
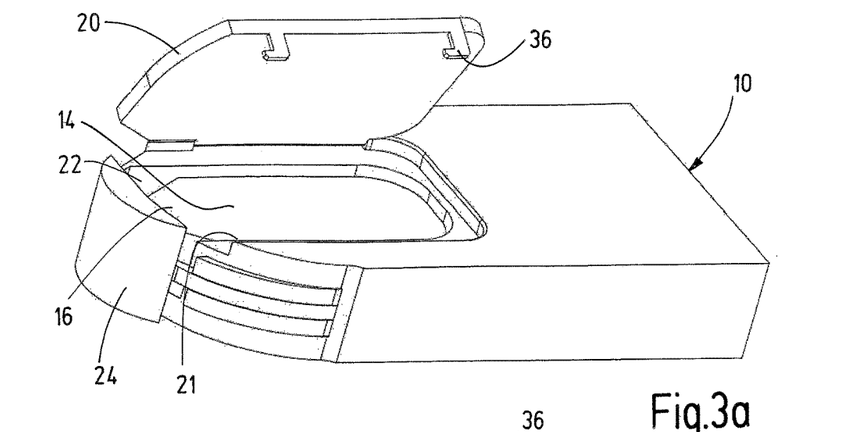
FIGS. 3a-3c show the glucose meter in a release position of the tip cover for opening the cassette door in views similar to FIG. 1.
Figure 3B:
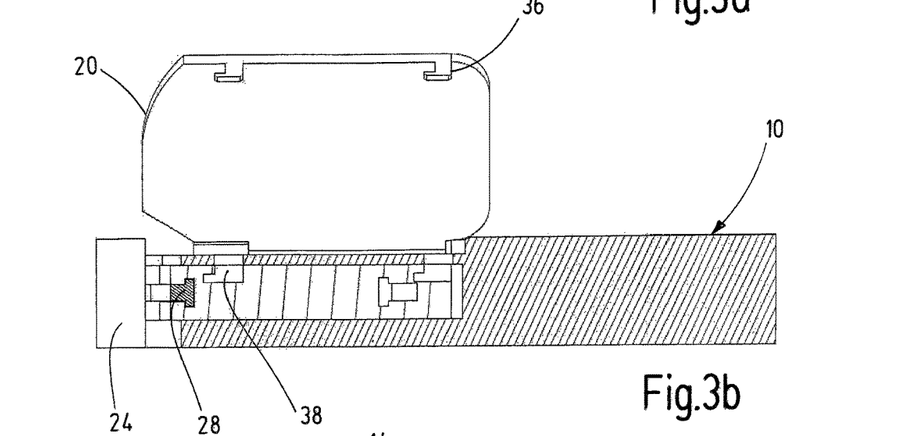
Figure 3C:
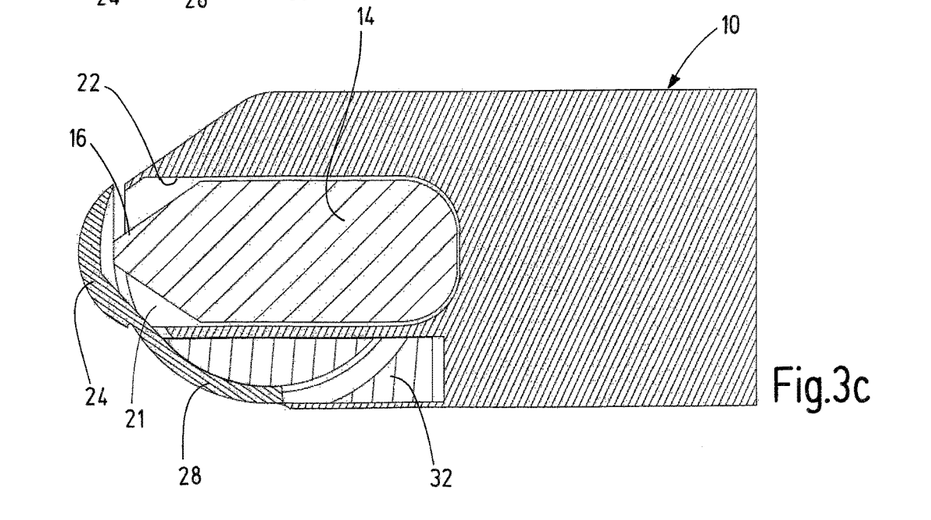

As illustrated in FIGS. 3a-c, the cassette 14 can be easily exchanged in a third (release) position of the tip cover 24. This position can be reached by manually gripping the tip cover 24 and exerting a pulling force, whereby the extension 28 extracts the guide block 32 out of the housing 12 along a limited distance defined by the recesses 38. In the open-end position, the retaining hooks 36 disengage the undercut and the cassette door 20 swings open under spring force. Then, the opening 21 of the cassette compartment 22 is extended into the area of the cassette tip 16 and the tape cassette 14 can be removed or exchanged without collision with the tip cover 24. Hence the tip cover 24 can be used as an operating element for both actuations, namely exposure of the sample application site and simultaneous opening of the cassette door 20 and tip cover 24.

Figures 4A, 4B:
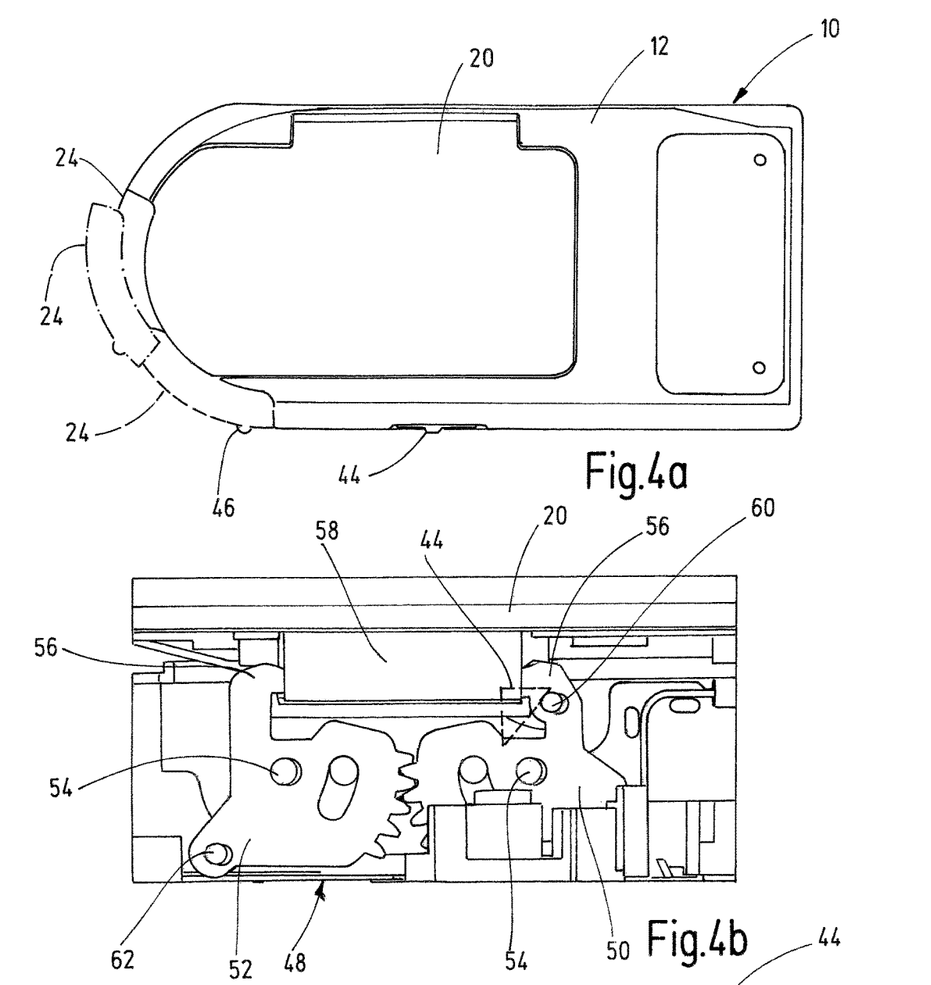
Figure 4C:
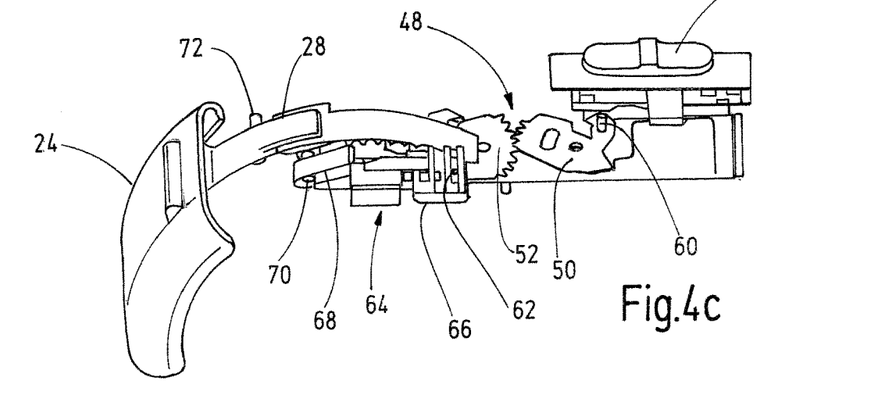
FIG. 4c is a perspective view of a mechanism of the glucose meter of FIG. 4a connecting a release button to a door lock.

FIGS. 4a-4c show an embodiment which allows simultaneous opening of the cassette door 20 and removal of the tip cover 24 for cassette exchange by means of a single one release button 44. The release button 44 can be manually operated as a sliding switch with the thumb of the hand holding the meter.

As illustrated in FIG. 4a the tip cover 24 can be moved into three positions. The arcuate movement between the closed position (solid line) and open position (dotted line) can be effected with the aid of a finger grasp 46 formed on the outer contour of the tip cover 24. The release position (dot and dash line) can be triggered via the release button 44, as further explained below.

FIG. 4b shows a lock module 48 for the cassette door 20. This module comprises two swing pinions 50, 52 which are swivel-mounted on respective bearing pins 54 such that locking hooks 56 can engage a holding part 58 on the inner side of the cassette door 20. Swing pinion 50 has a driving pin 60 connected to the release button 44. Swing pinion 52 has a linking pin 62 for actuating movement of the tip cover 24 into the third (release) position. When pushing the release button 44 (rightward as shown in FIG. 4b), the driving pin 60 on pinion 50 will rotate clockwise, effecting a counter-clockwise rotation of pinion 52 through tooth engagement. Then, the cassette door 20 will be released and swing open under spring force. Manual closing of the cassette door 20 will exert a force on the pinions 50, 52 to rotate in the locking direction.

FIG. 4c further elucidates a sliding module 64 next in line to the lock module 48 construed for movement of the tip cover 24 into the third (release) position. The sliding module 64 has a guide member 66 to transform the rotary motion of the linking pin 62 into a linear movement of a pulling member 68 acting on shaft 70. As the extension 28 of tip cover 24 has a pivot 72, the exerted pulling force promotes the tip cover 24 to swivel out to the position shown in dot and dash line in FIG. 4a. Thus, the tip cover 24 opens at the same time as the cassette door 20, and the cassette 14 is accessible to be replaced conveniently without collision.

FIGS. 5a-5d illustrate a design in which the tip cover 24 is movable on a guide structure 74, which in turn is mounted on a slider 76 that can be displaced relative to the housing 12 by means of a manually operated grip member 78.

Figure 5A:
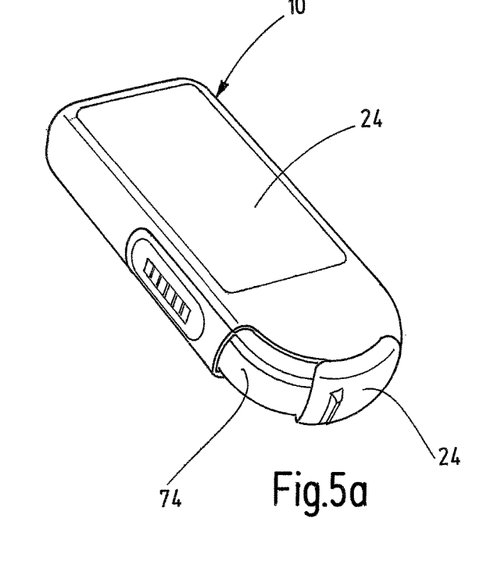
FIGS. 5a-5d show perspective views of a further embodiment of a glucose meter with a sliding release mechanism.
Figure 5B:
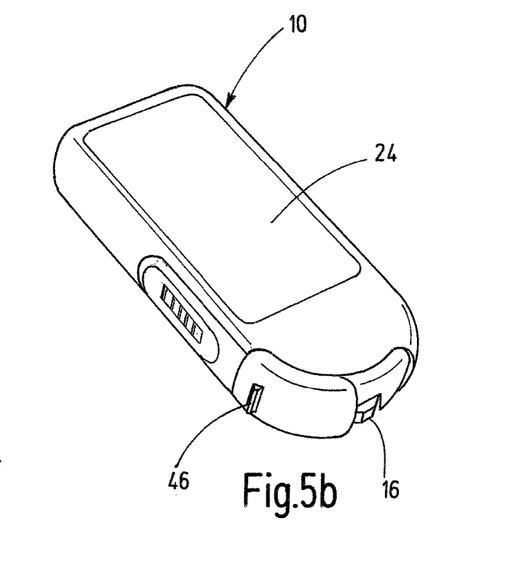
Figure 5C:
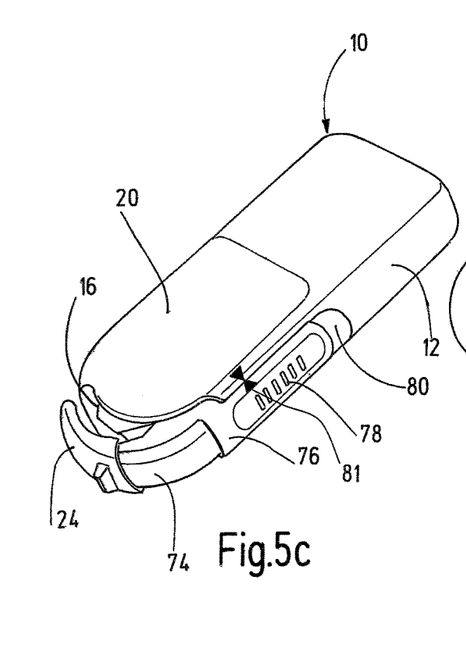
Figure 5D:
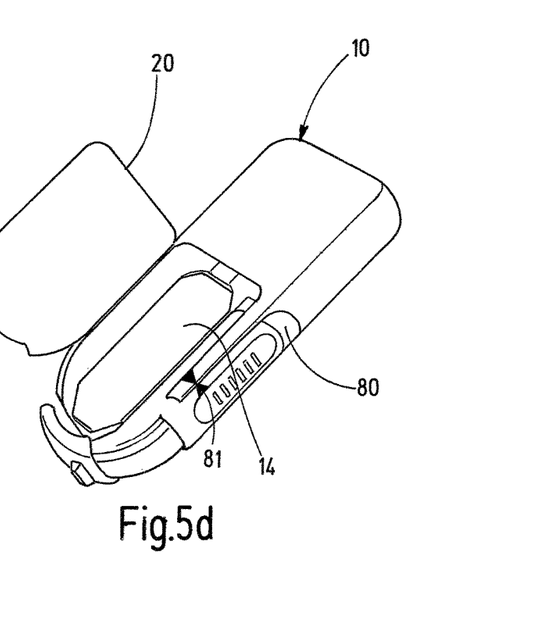

FIG. 5a shows the tip cover 24 in the closed state (first position), where the cassette door 20 is also closed and the meter 10 is in sleeping mode. For normal operation, the tip cover 24 can be moved by aid of finger grasp 46 along guide structure 74 to assume the open state (second position), as shown in FIG. 5b. In this working mode of the meter 10, the cassette tip 16 is accessible for sample application and optical measurement. As can be seen from FIG. 5c, the tip cover 24 can be transported to a third position where the cassette tip 16 is laterally exposed. The manually operated grip member 78 allows a corresponding linear shifting of the slider 76 in a track 80 of the housing 12. As explained before, the movement of the slider 76 also releases a door lock, e.g., retaining hooks 36, such that the cassette door 20 automatically opens and the cassette 14 can be replaced (FIG. 5d).

In order to assist the user in accurate positioning, the intended end positions can be marked by position marks 81 or pictograms provided on the housing and on the tip cover 24 and/or the slider 76. Then, the user is aware of the range of movement and the second and third positions can be located precisely specifically if the movement requires several steps in one direction.

Figure 6A:
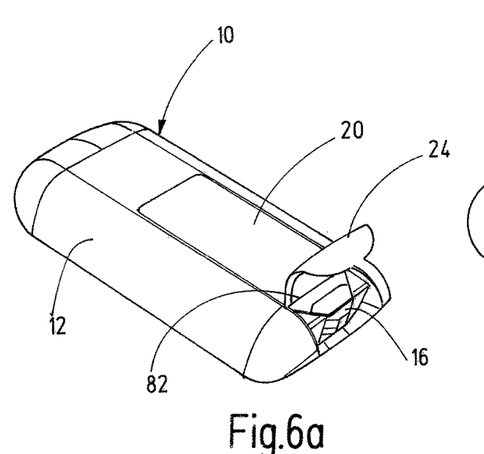
FIGS. 6a-6b show perspective views of a still further embodiment of a glucose meter with a combination door and tip cover.
Figure 6B:
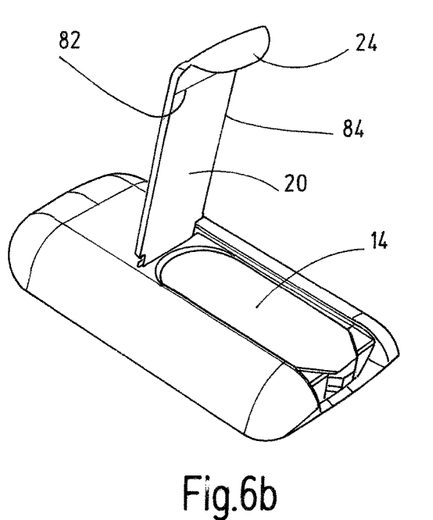
Figure 7:
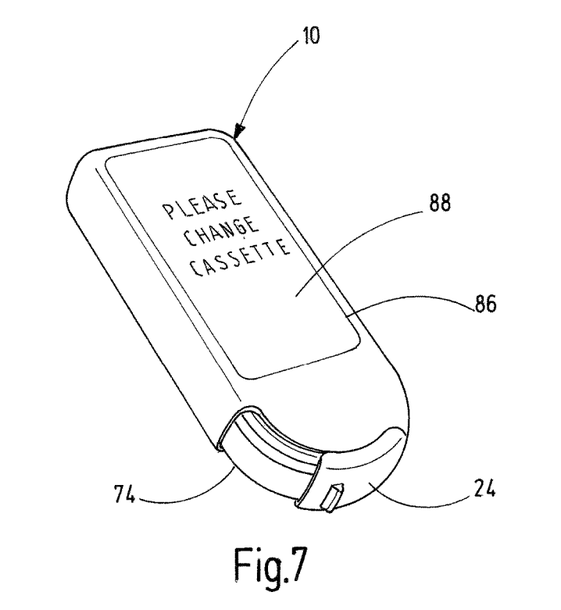
FIG. 7 shows an alternative embodiment of a glucose meter with an electronically controlled cassette door.

FIGS. 6a and 6b show an embodiment in which the tip cover 24 is connected to a lateral edge of the cassette door 20 via a hinge 82 to allow movement between the first and second position (FIG. 6a), and in which the cassette door 20 and the tip cover 24 can be moved cooperatively as a unitary lid 84 to move the cassette door 20 to the open position and the tip cover 24 to the third position (FIG. 6b).

FIG. 6 illustrates another embodiment of a glucose meter 10 having a tip cover that can be manually displaced on a guide structure 74 between first and second positions as also shown in FIGS. 5a and b. The meter 10 further comprises a device electronics 86 that is configured to prompt the user to open the tip cover 24 for a cassette change. For this purpose, device electronics 86 is adapted to detect conditions for replacement of the tape cassette, e.g., a consumed number of tests, a defect of the cassette 14, expiry of a life period of the cassette 14. Such a prompt can be shown on display 88, and then the device electronics 86 automatically unlocks the cassette door in the open position of the tip cover 24.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

What is claimed is:

1. A test tape device, comprising:
   a housing having a cassette compartment adapted to receive a replaceable analytical tape cassette;
   a cassette door having a door lock which can retain the cassette door in a closed position, the cassette door having an open position that allows access to the cassette compartment through a housing opening;
   a tip cover which can be positioned in a first position, a second position and a third position, wherein:
     in the first position the tip cover covers a housing aperture;
     in the second position the tip cover allows access to a cassette tip of the tape cassette that protrudes through the housing aperture for sample application;
     in the third position the cassette tip is at least partially uncovered and the housing opening is enlarged in the area of the cassette tip; and
     wherein the cassette door is self-opening when moving the tip cover to the third position.

2. Test tape device according to claim 1, wherein the door lock automatically unlocks when moving the tip cover to the third position.

3. Test tape device according to claim 2, wherein the door lock can be unlocked by a manually activated release button that is mechanically connected to the tip cover to actuate a movement to the third position.

4. Test tape device according to claim 3, further comprising a sliding module connected to the release button, wherein the tip cover is pivotable from the first position to the third position by a force of the sliding module.

5. Test tape device according to claim 1, wherein the tip cover can be manually operated to assume the third position and forms a leverage to actuate the door lock.

6. Test tape device according to claim 5, wherein a pivot is provided to allow pivoting of a free end of the tip cover.

7. Test tape device according to claim 1, wherein the tip cover is movable in a guide structure between the first and second positions, wherein the guide structure is mounted on a slider which is movable relative to the housing, wherein a movement of the slider carries the tip cover to the third position and unlocks the door lock.

8. Test tape device according to claim 7, further comprising a grip member formed on the slider for shifting of the slider in a linear track of the housing.

9. Test tape device according to claim 1, wherein the tip cover is moveably connected to the cassette door to allow movement between the first and second positions, and wherein the cassette door and the tip cover can be moved cooperatively as a unitary lid to move the cassette door to the open position and the tip cover to the third position.

10. Test tape device according to claim 9, further comprising a hinge mounted between an edge of the cassette door and an edge of the tip cover.

11. Test tape system comprising a test tape device of claim 1 and further comprising an analytical tape cassette including a test tape inserted in the cassette compartment.

12. Test tape device, comprising:
   a housing having a cassette compartment adapted to receive a replaceable analytical tape cassette;

a cassette door which can be locked in a closed position, the cassette door having an open position allowing access to the cassette compartment through a housing opening;

a tip cover which can be positioned in a first position covering a housing aperture and a second position allowing access to a tip of the tape cassette arranged to protrude through the housing aperture for sample application; and device electronics configured to prompt the user to open the tip cover for a cassette change and to automatically unlock the cassette door in the open position of the tip cover.

13. Test tape device according to claim 12, wherein the device electronics is adapted to detect conditions for replacement of the tape cassette.

14. Test tape system comprising a test tape device of claim 12 and further comprising an analytical tape cassette including a test tape inserted in the cassette compartment.

15. Method for operating a test tape device having a cassette compartment with a cassette door and a movable tip cover, the method comprising:

positioning the tip cover in a first position for covering a housing aperture;

moving the tip cover to a second position to allow access to a tip of the tape cassette for sample application;

moving the tip cover to a third position in which the cassette tip is at least partially uncovered and the housing opening is enlarged in the area of the cassette tip, wherein the cassette door self-opens when moving the tip cover to the third position; and inserting or replacing the tape cassette in the third position of the tip cover.

16. Method according to claim 15, further comprising providing the tip cover as an actuation element for automatically releasing a door lock of the cassette door in the third position.

* * * * *